(12) United States Patent
Miyata et al.

(10) Patent No.: US 9,345,253 B2
(45) Date of Patent: May 24, 2016

(54) METAL SOAP FOR ADDITION TO FOOD AND PROCESS FOR PRODUCTION THEREOF

(75) Inventors: Yasuyuki Miyata, Hyogo (JP); Masahiro Fukumoto, Hyogo (JP); Noriko Fujio, Hyogo (JP); Nobuhiko Shizuka, Hyogo (JP)

(73) Assignee: NOF CORPORATION, Tokyo (JP)

( * ) Notice: Subject to any disclaimer, the term of this patent is extended or adjusted under 35 U.S.C. 154(b) by 1646 days.

(21) Appl. No.: 11/997,186

(22) PCT Filed: Jul. 31, 2006

(86) PCT No.: PCT/JP2006/315156
§ 371 (c)(1),
(2), (4) Date: May 7, 2010

(87) PCT Pub. No.: WO2007/013655
PCT Pub. Date: Feb. 1, 2007

(65) Prior Publication Data
US 2010/0215821 A1 Aug. 26, 2010

(30) Foreign Application Priority Data

Jul. 29, 2005 (JP) ................................. 2005-220226
Jan. 13, 2006 (JP) ................................. 2006-006665

(51) Int. Cl.
*A23L 1/03* (2006.01)
*C07C 51/00* (2006.01)

(52) U.S. Cl.
CPC *A23L 1/032* (2013.01); *C07C 51/00* (2013.01)

(58) Field of Classification Search
None
See application file for complete search history.

(56) References Cited

U.S. PATENT DOCUMENTS 5,356,544 A * 10/1994 Zilberman et al. ............ 508/527
2003/0030028 A1* 2/2003 Nakata ............................ 252/69

FOREIGN PATENT DOCUMENTS

| EP | 429 692 | 6/1991 |
|---|---|---|
| GB | 2113521 | 8/1983 |
| JP | 52-068883 | 6/1977 |
| JP | 62-41658 | 9/1987 |
| JP | 02-006428 | 1/1990 |
| JP | 02-178250 | 7/1990 |
| JP | 04-066551 | 3/1992 |
| JP | 2005-213217 | 8/2005 |

OTHER PUBLICATIONS

English Machine Translation of JP 2005-213217.*
Extended European Search Report, including Supplementary European Search Report and Search Opinion, dated Nov. 18, 2009, for Application No. EP 06 78 2034.
G. Poulenat, et al., "Double Decomposition Reactions for the Production of Alkaline and Alkaline-Earth Oleic Soaps under Salting-Out Conditions", *Ind. Eng. Chem. Res.*, vol. 43, 2004, pp. 1574-1579.
M. F. R. Fouda, et al., "Thermal stability of some metal-palmitate soaps which find various industrial applications", *Grasas y Aceites*, vol. 52, Fasc. 5 (2001), pp. 317-322.

* cited by examiner

*Primary Examiner* — David J Blanchard
*Assistant Examiner* — Sarah Chickos
(74) *Attorney, Agent, or Firm* — Oblon, McClelland, Maier & Neustadt, L.L.P.

(57) ABSTRACT

There are provided a metal soap which is useful as a food additive to be added to various foods for the purposes of improving a fluidity, an anti-bridging property, a low moisture absorption property and feel upon eating of foods, and has a less adverse influence on the foods, as well as a process for producing the metal soap. The metal soap for a food additive is constituted of a fatty acid calcium salt or a fatty acid magnesium salt having 6 to 24 carbon atoms which is obtained by a double decomposition method, and a water dispersion containing the metal soap in an amount of 2% by mass exhibits a pH of not less than 6 but less than 7. The process for producing the metal soap for a food additive includes the steps of reacting 1 mol of a fatty acid having 6 to 24 carbon atoms with not less than 0.9 mol but less than 1 mol of a monovalent basic compound to obtain a fatty acid basic compound salt; and reacting the fatty acid basic compound salt with a calcium salt or a magnesium salt in an aqueous medium.

14 Claims, No Drawings

METAL SOAP FOR ADDITION TO FOOD AND PROCESS FOR PRODUCTION THEREOF

TECHNICAL FIELD

The present invention relates to metal soaps useful as a food additive, and more particularly to fatty acid calcium salts or fatty acid magnesium salts having a less adverse influence on foods and a process for producing the same.

BACKGROUND ART

Metal soaps have been industrially produced by a direct method in which a fatty acid is directly reacted with a metal oxide or a metal hydroxide, or by a double decomposition method in which a fatty acid and a basic compound are mixed and reacted with each other in the form of an aqueous solution to obtain a fatty acid basic compound salt, and then the thus obtained fatty acid basic compound salt is further reacted with a metal salt.

In the direct method, the fatty acid and the metal compound are maintained at a temperature not less than a melting point of a metal soap produced therefrom, under a solvent-free condition, so that the reaction therebetween proceeds while evaporating off water produced during the reaction out of the reaction system to thereby produce the metal soap.

The direct method have problems such as prolonged reaction time, discoloration of the metal soap owing to thermal degradation and high contents of free fatty acid and unreacted metal compound in the resultant metal soap. To solve these problems, there has been proposed the process for producing a metal soap in which a fatty acid is melted in a heating-type kneading reactor, and a metal oxide or a metal hydroxide containing water of crystallization or water adsorbed is gradually added to the molten fatty acid to allow these components to react with each other under a solvent-free condition at a temperature near a melting point of the aimed metal soap while removing water produced from the reactor (see, for example, Patent Document 1).

However, in the process proposed by the above Patent Document 1, as described in Example 2 thereof, since the amount of calcium hydroxide added is as large as 0.55 mol per mole of the fatty acid (1.1 equivalents based on the fatty acid), there still remains a fear that the obtained metal soap contains a large amount of unreacted metal compound. Therefore, the metal soap obtained by the above process tends to be unsuitable as a food additive.

On the other hand, the double decomposition method has advantages such as a less content of free fatty acid in the obtained metal soap, facilitated dispersion of the metal soap due to fine particle size thereof, a less inclusion of different kinds of metals in the metal soap. However, these advantages usually depend upon such a production process in which a large amount of water must be used to complete the reaction, and an excess amount of the raw material which can be readily removed by purification must be charged into the reaction system in order to enhance a purity of the obtained metal soap.

More specifically, in a neutralization step for obtaining the fatty acid basic compound salt, an excess amount of the basic compound is reacted with an equivalent amount of the fatty acid.

In addition, there has also been proposed the process for producing a metal soap having a large particle size by a double decomposition method in which the aimed fatty acid metal soap is previously dispersed in an aqueous solution of a fatty acid alkali metal salt or a fatty acid ammonium salt and subjected to crystal growth to increase a particle size thereof (see, for example, Patent Document 2).

In the double decomposition method proposed by Patent Document 2 which aims at increasing a particle size of the metal soap, sodium hydroxide is reacted with the fatty acid such that the amount of sodium hydroxide used is 1.08 mol on the average per mole of the fatty acid in terms of the data described in Examples 1 to 3 thereof to obtain a fatty acid sodium salt, and then the sodium salt is further reacted with calcium chloride to obtain the aimed metal soap. Thus, in the conventional double decomposition processes, an excess amount of the basic compound has been reacted with an equivalent amount of the fatty acid.

In U.S. and European countries, the metal soaps have been used as a food additive and applied to extensive foods for the purposes of improving a moldability of foods obtained by compression-molding a powdery material into a desired shape, a fluidity of foods put on the market in the form of a powder such as a wheat flour and condiments, and an anti-aging property of bakery foods.

In Japan, the use of a fatty acid calcium salt and a fatty acid magnesium salt in foods has been past prohibited, but permitted on December, 2004 and January, 2004, respectively. As a result, the application of these salts to various foods as well as studies thereon have been now commenced.

However, the conventional metal soaps which have been contemplated to enhance a purity thereof tend to exhibit an alkalinity within a pH range of about 9 to 11 when contacted with water, since those produced by the direct method contains a large amount of residual metal oxide and metal hydroxide whereas those produced by the double decomposition method requires the use of an excess amount of a basic compound. For this reason, when the metal soaps are used as a food additive, there tends to arise such a problem that foods containing pigments, etc., suffer from discoloration when preserved for a long period of time.

Also, in the direct method, even when the reaction is conducted by using an excess amount of the fatty acid, the raw metal oxide or metal hydroxide is not completely consumed and remained unreacted owing to a low reaction rate thereof. As a result, there still remains the above problem that the metal soaps exhibit an alkalinity when contacted with water.

As described above, there have been conventionally proposed neither metal soaps having a less adverse influence on foods when added thereto as a food additive nor production process thereof.

Patent Document 1: Japanese Patent Application Laid-open No. 66551/1992.

Patent Document 2: Japanese Patent Publication No. 41658/1987.

DISCLOSURE OF THE INVENTION

An object of the present invention is to provide a metal soap having a less adverse influence on foods which is useful as a food additive for improving a fluidity, an anti-bridging property, a low moisture absorption property and feel upon eating of the foods, as well as a process for producing the metal soap.

As a result of intensive and extensive researches to solve the above problems, the inventors have found that a metal soap composed of a fatty acid calcium salt or a fatty acid magnesium salt which is suitable as a food additive having a less adverse influence on foods, can be produced by such a double decomposition method in which a fatty acid is first reacted with a basic compound at a specific molar ratio in which the fatty acid is present in an excess amount relative to the basic compound, to obtain a fatty acid basic compound salt, and then the fatty acid basic compound salt is further reacted with a calcium salt or a magnesium salt. Further, it has been found that the thus produced metal soap exhibits a pH value of no alkalinity even when dispersed in water. The present invention has been accomplished on the basis of the finding.

Thus, the present invention provides:

(1) A metal soap for a food additive comprising a fatty acid calcium salt or a fatty acid magnesium salt having 6 to 24 carbon atoms which is produced by a double decomposition method, wherein a water dispersion containing said metal soap in an amount of 2% by mass exhibits a pH of not less than 6 but less than 7.

(2) A process for producing a metal soap for a food additive by a double decomposition method, wherein said metal soap comprises a fatty acid calcium salt or a fatty acid magnesium salt having 6 to 24 carbon atoms, and a water dispersion containing said metal soap in an amount of 2% by mass exhibits a pH of not less than 6 but less than 7, said process comprising:

reacting 1 mol of a fatty acid having 6 to 24 carbon atoms with not less than 0.9 mol but less than 1 mol of a monovalent basic compound to obtain a fatty acid basic compound salt; and reacting the resultant fatty acid basic compound salt with a calcium salt or a magnesium salt in an aqueous medium.

(3) The process as described in the above aspect (2), wherein the calcium salt or the magnesium salt is reacted in an amount of 0.4 to 0.6 mol per 1 mol of the fatty acid used.

The metal soap of the present invention exhibits a less adverse influence on foods when added thereto as a food additive, has excellent effects of improving a fluidity, an anti-bridging property and a low moisture absorption property of powdery foods, a moldability upon forming tablets, and feel upon eating, shows a good storage stability without discoloration, and is excellent in safety when used as a food additive.

Also, in the process for producing a metal soap according to the present invention, the metal soap of the present invention which is useful as a food additive can be produced in a stable manner with a high productivity.

BEST MODES FOR CARRYING OUT THE INVENTION

The present invention is described in detail below.

The metal soap for a food additive according to the present invention is composed of a fatty acid calcium salt or a fatty acid magnesium salt having 6 to 24 carbon atoms which is produced by a double decomposition method, and a water dispersion containing the metal soap in an amount of 2% by mass exhibits a pH of not less than 6 but less than 7.

According to the process of the present invention, the metal soap of the present invention can be efficiently produced by reacting a fatty acid basic compound salt obtained by reacting 1 mol of a fatty acid having 6 to 24 carbon atoms with not less than 0.9 but less than 1 mol of a monovalent basic compound, with a calcium salt or a magnesium salt in an aqueous medium by a double decomposition method, and then dehydrating and drying the resultant metal soap slurry. These metal soaps may be added to foods alone or in combination of any two or more thereof.

Examples of the fatty acid having 6 to 24 carbon atoms usable in the present invention include linear fatty acids suitably used in foods, such as caproic acid, caprylic acid, capric acid, lauric acid, myristic acid, palmitic acid, oleic acid, linoleic acid, linolenic acid, stearic acid, arachic acid, erucic acid and behenic acid. Among these fatty acids, preferred are linear saturated fatty acids having 12 to 22 carbon atoms.

When using fatty acids having less than 6 carbon atoms, the resultant metal soap tends to fail to improve a fluidity or a moldability of foods when added thereto. On the other hand, fatty acids having more than 24 carbon atoms tend to be industrially unavailable. These fatty acids may be used alone or in combination of any two or more thereof.

Examples of the monovalent basic compound usable in the present invention include monovalent alkali metal hydroxides such as sodium hydroxide and potassium hydroxide, and ammonium compounds such as ammonia, triethylamine, triethanolamine, diethanolamine and monoethanolamine.

Among these monovalent basic compounds, in view of formation of fatty acid salts having a good solubility in water, preferred are sodium hydroxide and potassium hydroxide. These basic compounds may be used alone or in combination of any two or more thereof.

The fatty acid basic compound salt may be produced by reacting the fatty acid with the basic compound in an aqueous medium at such a molar ratio in which the basic compound is used in an amount of not less than 0.9 but less than 1, preferably from 0.92 to 0.99 mol and more preferably from 0.93 to 0.98 mol per 1 mol of the fatty acid.

Among these fatty acid basic compound salts, especially preferred are those salts which are obtained by reacting the fatty acid with the basic compound at such a molar ratio in which the basic compound is used in an amount of 0.95 to 0.98 mol per 1 mol of the fatty acid in the case where the fatty acid basic compound salt is reacted with a calcium salt, and those salts which are obtained by reacting the fatty acid with the basic compound at such a molar ratio in which the basic compound is used in an amount of 0.93 to 0.96 mol per 1 mol of the fatty acid in the case where the fatty acid basic compound salt is reacted with a magnesium salt. When the amount of the basic compound charged is out of the above-specified range, the resultant metal soap tends to exert an adverse influence on foods when added thereto, or a yield of the metal soap tends to become lowered.

The concentration of the fatty acid basic compound salt used in the double decomposition reaction system is usually 1 to 20% by mass and preferably 5 to 15% by mass from the standpoints of good productivity of the metal soap and good handling property of the reaction solution.

When the concentration of the fatty acid basic compound salt used in the double decomposition reaction system is 1% by mass or more, the metal soap can be produced with a practically effective yield, whereas when the concentration of the fatty acid basic compound salt used in the double decomposition reaction system is 20% by mass or less, an aqueous solution of the fatty acid basic compound salt or the metal soap slurry can exhibit an adequate viscosity, thereby enabling a homogeneous reaction.

The temperature of the reaction when conducted at the above molar ratio is usually a temperature not lower than a melting point of the fatty acid, i.e., such a temperature at which the fatty acid is inhibited from being decomposed, preferably 100° C. or lower, more preferably 50 to 100° C. and still more preferably 75 to 95° C.

The calcium salt or the magnesium salt usable in the double decomposition step of the present invention is not particularly limited as long as it is a water-soluble neutral salt. Examples of the calcium salt or the magnesium salt include calcium chloride, magnesium chloride, calcium nitrate and magnesium sulfate. Among these metal salts, in view of good solubility in water, high solubility of by-produced salts and good applicability to food additives, preferred are calcium chloride, calcium nitrate and magnesium sulfate. These metal salts may be used alone or in combination of any two or more thereof.

The double decomposition reaction for obtaining the metal soap from an aqueous solution of the fatty acid basic compound salt may be usually conducted by separately preparing an aqueous solution of the above metal salt and then mixing the thus prepared aqueous metal salt solution with the aqueous solution of the fatty acid basic compound salt. For example, the aqueous metal salt solution may be dropped to the aqueous solution of the fatty acid basic compound salt or the aqueous solution of the fatty acid basic compound salt may be dropped to the aqueous metal salt solution, or both of the aqueous metal salt solution and the aqueous solution of the fatty acid basic compound salt may be dropped in a reaction vessel at the same time.

The concentration of the metal salt in the aqueous metal salt solution is usually 1 to 50% by mass and preferably 10 to 40% by mass from the standpoints of good yield of the metal soap and good handling property of the reaction solution.

In the double decomposition step, the respective raw materials are charged at such a molar ratio in which the calcium salt or the magnesium salt is added in an amount of preferably 0.4 to 0.6 mol and more preferably 0.45 to 0.55 mol per 1 mol of the fatty acid used for producing the fatty acid basic compound salt, and then reacted with each other in an aqueous medium to thereby obtain the metal soap aimed by the present invention. When the molar ratio of the metal salt lies within the range of 0.4 to 0.6 mol, the metal soap can be produced with a good yield, and the resultant metal soap can exhibit a good quality.

The double decomposition reaction may be conducted under temperature conditions usually employed by the person with ordinary skill in the art in view of the solubility of the fatty acid basic compound salt and the double decomposition reaction temperature is preferably 50 to 100° C. and more preferably 75 to 95° C.

The thus obtained metal soap slurry is subjected to filtration using a filtering equipment such as a filter press to remove water therefrom and thereby obtain a dehydrated cake, and further subjected to washing, if required, to remove salts by-produced during the reaction. Further, the dehydrated cake may be subjected to drying treatment using a flush dryer or an air blast dryer, and then to pulverization, if required, thereby obtaining the metal soap of the present invention.

Thus, the metal soap of the present invention is produced via the fatty acid basic compound salt produced by reacting the fatty acid with the basic compound at such a molar ratio in which the fatty acid is used in an excess amount relative to the basic compound. As a result, a water dispersion containing the metal soap in an amount of 2% by mass has a pH of not less than 6 but less than 7, i.e., exhibits no alkalinity. The pH of the water dispersion is more preferably 6.3 to 6.9.

The above pH used in the present invention means the value obtained by measuring a pH of a water dispersion of the metal soap which is prepared by dispersing 2% by mass of the metal soap in ion-exchanged water using a nonionic surfactant having no influence on the pH. Examples of the nonionic surfactant include polyethylene glycol-based nonionic surfactants having a HLB value of 12 to 15. Among these polyethylene glycol-based nonionic surfactants, in view of good dispersion stability, preferred are those having a HLB value of about 13 such as polyoxyethylene (10 mol) nonylphenyl ether and polyoxyethylene (9 mol) tridecyl ether.

Examples of the foods to which the metal soap of the present invention can be added, include cereals such as wheat flour and starches as well as premixes obtained by blending butter or sugar in these cereals, condiments such as red pepper, seasonings such as sodium glutamate, extracts obtained from fruit skins of citrus, pigments for foods such as red perilla, noodles such as wheat vermicelli, bakery foods such as breads, fried foods such as doughnuts, and confectioneries such as biscuits, candies and chewing gums.

Further, in addition to the metal soap of the present invention, these foods may appropriately contain other food additives. Examples of the other food additives include sweeteners, colorants, preservatives, thickening stabilizers, antioxidants, bitterns, brightening agents, sour condiments, seasonings, emulsifying agents, swelling agents and reinforcing agents.

EXAMPLES

The present invention will be described in more detail by referring to the following examples. However, it should be noted that these examples are only illustrative and not intended to limit the invention thereto.

<Production of Metal Soap>

Using two kinds of mixed fatty acids respectively having a composition shown in Table 1, Examples 1 to 3 were conducted to obtain metal soaps of the present invention, and Comparative Examples 1 and 2 were conducted to obtain comparative metal soaps. The compositions of alkyl groups of the respective fatty acids are also shown in Table 1.

The mixed fatty acid A was composed of 66% by mass of stearic acid, 31% by mass of palmitic acid, 2% by mass of myristic acid and 1% by mass of arachidic acid, and the mixed fatty acid B was composed of 99% by mass of lauric acid and 1% by mass of myristic acid.

TABLE 1

| | Number of carbon atoms | | | | | | Molecular |
|---|---|---|---|---|---|---|---|
| | 12 | 14 | 16 | 18 | 20 | Total | weight |
| Fatty acid A (mass %) | — | 2 | 31 | 66 | 1 | 100 | 272 |
| Fatty acid B (mass %) | 99 | 1 | — | — | — | 100 | 200 |

Example 1

A 5 L glass flask was charged with 3000 g of tap water and then with 245 g (0.9 mol) of the fatty acid A, and the contents of the flask were heated to 90° C. Then, while stirring the contents of the flask, 73 g of a 48% by mass sodium hydroxide aqueous solution (0.88 mol; corresponding to 0.98 mol per 1 mol of the fatty acid) was added into the flask for 30 min, and the contents of the flask were continuously stirred at 90° C. for 1 h, thereby obtaining an aqueous solution of a fatty acid sodium salt.

Next, 149 g of a 35% by mass calcium chloride aqueous solution [0.47 mol; corresponding to 0.52 mol (1.04 equivalent) per 1 mol of the fatty acid] was added while stirring to the thus obtained aqueous solution of the fatty acid sodium salt for 30 min. After completion of the addition, the resultant mixture was continuously stirred at 90° C. for 1 h to obtain a fatty acid calcium salt slurry. The thus obtained fatty acid calcium salt slurry was cooled to 70° C., and then subjected to filtration using a suction filter. Further, 3000 g of tap water was poured on the filter from above to wash the resultant filter cake composed of the fatty acid calcium salt, and then the fatty acid calcium salt cake was dried at 80° C. for 36 h within an air blast dryer, thereby obtaining a fatty acid calcium salt (Y-1).

Example 2

A 5 L glass flask was charged with 3000 g of tap water and then with 180 g (0.9 mol) of the fatty acid B, and the contents of the flask were heated to 90° C. Then, while stirring the contents of the flask, 120 g of a 40% by mass potassium hydroxide aqueous solution (0.86 mol; corresponding to 0.96 mol per 1 mol of the fatty acid) was added into the flask for 30 min, and then the contents of the flask were continuously stirred at 90° C. for 1 h, thereby obtaining an aqueous potassium laurate solution.

Next, 140 g of a 35% by mass calcium chloride aqueous solution [0.44 mol; corresponding to 0.49 mol (0.98 equivalent) per 1 mol of the fatty acid] was added while stirring to the thus obtained aqueous potassium laurate solution for 30 min. After completion of the addition, the resultant mixture was continuously stirred at 90° C. for 1 h to obtain a calcium laurate slurry. The thus obtained calcium laurate slurry was cooled to 70° C., and then subjected to filtration using a suction filter. Further, 3000 g of tap water was poured on the filter from above to wash the resultant filter cake composed of calcium laurate, and then the calcium laurate cake was dried at 80° C. for 36 h within an air blast dryer, thereby obtaining calcium laurate (Y-2).

Example 3

A 5 L glass flask was charged with 3000 g of water and 245 g (0.9 mol) of the fatty acid A, and the contents of the flask were heated to 70° C. while stirring. Then, 71 g of a 48% by mass sodium hydroxide aqueous solution (0.85 mol; corresponding to 0.94 mol per 1 mol of the fatty acid) was charged into the flask, and the contents of the flask were continuously stirred at 70° C. for 30 min, thereby obtaining an aqueous solution of a fatty acid sodium salt. In addition, 165 g of a 35% by mass magnesium sulfate aqueous solution [0.47 mol; corresponding to 0.53 mol (1.06 equivalent) per 1 mol of the fatty acid) was dropped into the flask at 70° C. for 1 h. After completion of the dropping, the resultant mixture was heated to 80° C. and continuously stirred for 1 h to obtain a fatty acid magnesium salt slurry. The thus obtained slurry was cooled to 60° C. or lower and then charged into a centrifugal dehydrator having a diameter of 30 cm for dehydration thereof, and at the same time, 5000 g of tap water was added into the dehydrator to wash a cake therein. The resultant dehydrated cake was dried at 60° C. for 60 h, thereby obtaining a fatty acid magnesium salt (Y-3).

Comparative Example 1

The same procedure as in Example 1 was repeated except that the amount of the 48% by mass sodium hydroxide aqueous solution used was changed to 79 g (0.95 mol; corresponding to 1.05 mol per 1 mol of the fatty acid), and the amount of the 35% by mass calcium chloride aqueous solution used was changed to 159 g [0.50 mol; corresponding to 0.56 mol (1.11 equivalent) per 1 mol of the fatty acid], thereby obtaining a fatty acid calcium salt (Z-1).

Comparative Example 2

A 5 L glass flask was charged with 245 g (0.9 mol) of the fatty acid A and 3000 g of tap water, and the contents of the flask were heated to 80° C. while stirring. Then, 32 g of potassium hydroxide (0.43 mol; corresponding to 0.48 mol, i.e., 0.96 equivalent, per 1 mol of the fatty acid) was added to the flask at 80° C. for 30 min. After completion of the addition, the resultant mixture was heated to 90° C. and continuously stirred for 1 h to obtain a fatty acid calcium salt slurry. The thus obtained fatty acid calcium salt slurry was cooled to 60° C. and then filtered using a suction filter. Thereafter, the resultant filter cake was dried at 75° C. for 48 h, thereby obtaining a fatty acid calcium salt (Z-2) by a direct method.

<Analysis of Metal Soap>

The metal soaps obtained in Examples 1 to 3 and Comparative Examples 1 and 2 were analyzed by the following methods. The results are collectively shown in Table 2.

(A) Calcium or Magnesium Content

The calcium or magnesium content was measured by the method prescribed in the codex for food additives pursuant to Japanese Article 21 of Food Sanitation Law.

(B) Free Fatty Acid

Five grams of the metal soap was weighed and sampled in a beaker, and 50 g of a mixed solvent of diethyl ether and ethanol (mixed solution containing diethyl ether and ethanol at a volume ratio of 1:1) was added to the beaker. The contents of the beaker were stirred for 30 seconds and then allowed to stand for 30 min. Thereafter, the obtained mixture was filtered through a filter paper 5B, and the resultant filtrate was subjected to titration using a 0.1 N potassium hydroxide titrant to calculate a content of a free fatty acid therein according to the following formula (1). The same procedure was repeated using a fatty acid blank.

$$\text{Content of Free Fatty Acid}=(A-B)\times f\times M/W/100 \quad (1)$$

wherein A is an amount (mL) of titrant dropped to the sample; B is an amount (mL) of titrant dropped to the blank; f is a factor of the 0.1 N potassium hydroxide titrant solution; M is a molecular weight of the fatty acid used; and W is an amount (g) of the metal soap sampled.

(C) Loss in Weight on Drying

The loss in weight on drying was measured by the method prescribed in the codex for food additives mentioned above.

(D) pH of Water Dispersion Containing 2% by Mass of Metal Soap

In a laboratory maintained at 25° C., 2.0 g of the metal soap was weighed and sampled in a 100 mL beaker, and then 98.0 g of a 0.1% by mass aqueous solution prepared by diluting an oxyethylene (10 mol) nonylphenyl ether having a HLB value of 13.3 with ion-exchanged water was added to the beaker. The contents of the beaker were stirred until a uniform dispersion was obtained. The thus obtained dispersion was subjected to a pH measurement three times using a pH electrode to calculate an average of the three measured values.

(E) Average Particle Size of Metal Soap

An average particle size of each of the metal soaps obtained in Examples and Comparative Examples was determined by charging 0.5 g of each metal soap sample into an ethanol medium and measuring particle sizes thereof using a laser diffraction scattering-type particle size distribution meter "MICRO-TRACK MT-3000" available from Nikkiso Co., Ltd.

<Evaluation of Performance of Metal Soap as Food Additive>

(F-1) Moldability and Anti-Discoloration Property

Four hundred fifty grams of red perilla, 40 g of crystalline cellulose and 10 g of each of the metal soaps obtained in Examples and Comparative Examples was mixed with each other using a high-speed mixer. The obtained mixed particles were formed into 150 tablets using a single tableting machine with a mold having a diameter of 10 mm to evaluate a moldability thereof. The moldability was evaluated according to the following ratings:

A: No defects such as creaking during molding of 150 tablets and sticking and capping on a surface of each tablet;

B: No creaking during molding, but sticking was observed on the tablet after molding 150 tablets; and C: Creaking occurred immediately after initiation of molding, and any tablets was not moldable.

Further, after the obtained tablets were preserved at a temperature of 23° C. and a relative humidity of 50% RH for two months, an appearance thereof was observed. The appearance of the tablets was examined and evaluated according to the following ratings:

A: Substantially no discoloration was observed; and
B: Severe discoloration was observed.

The evaluation results are collectively shown in Table 2.
(F-2) Moldability and Keeping Property (Anti-Color Change Property)

One hundred grams of L-ascorbic acid (80-mesh product) available from BASF Takeda Vitamin Co., Ltd., 500 g of a reducing maltose starch syrup (multitol) available from Towa Kasei Co., Ltd., 150 g of crystalline cellulose "CEOLUS ST-02" available from Asahi Kasei Chemicals Co., Ltd., 150 g of lactose for tableting "SUPER TAB" available from Asahi Kasei Chemicals Co., Ltd., 50 g of a powdery lemon aroma and 20 g of each of the metal soaps obtained in Examples and Comparative Examples were mixed with each other using a 5 L high-speed mixer. The resultant mixture was molded into 1000 tablet-shaped candies each having a diameter of 7 mm and a thickness of 3 mm using a rotary continuous tableting machine. The thus obtained candies had a while color. Meanwhile, tablet-shaped candies containing no metal soap were also prepared as a blank.

The moldability was evaluated by observing an appearance of the molded product upon molding 1000 tablets by naked eyes, and the keeping property (anti-color change property) was evaluated by observing a change in color tone of the tablets by naked eyes after preserved at a temperature of 40° C. and a relative humidity of 60% RH for one month.

The ratings for each evaluation are as follows:
Evaluation of Moldability

A: No sticking occurred upon molding of 1000 tablet-shaped candies, and the surface of each tablet was smooth;

B: Sticking occurred upon molding of 1000 tablet-shaped candies; and

C: Severe creaking occurred upon tableting, and 1000 tablets were not moldable.
Evaluation of Keeping Property A: No color change occurred on the tablet-shaped candies after keeping test;

B: Slight color change occurred on the tablet-shaped candies after keeping test; and C: Severe yellow discoloration occurred on the tablet-shaped candies after keeping test.

The evaluation results are collectively shown in Table 2.
(G) Evaluation of Fluidity and Change in Hue Due to Heating One gram of each of the metal soaps obtained in Examples and Comparative Examples was added to 80 g of a dried powder of orange fruit skin (particle size: 90% pass: 200 μm or less) and 20 g of sugar (high-quality sugar; particle size: 90% pass: 150 μm or less), and these components were mixed with each other until a uniform mixture was obtained. The thus obtained mixture was charged into a funnel, and the funnel was shaken at an amplitude of 0.4 mm and a frequency of 60 Hz to drop the mixture therefrom and form a deposit. The angle of repose of the thus obtained deposit was measured using a powder tester available from Hosokawa Micron Co., Ltd., to examine a fluidity thereof. The fluidity was evaluated according to the following ratings:

A: Angle of repose of the deposit was less than 55°;

B: Angle of repose of the deposit was not less than 55° but less than 57.5°; and C: Angle of repose of the deposit was 57.5° or more.

Further, 50 g of water was added to 50 g of the above mixture. The resultant mixture was charged into an aluminum pan and weakly heated until a transparent viscous liquid was obtained to observe a hue of the viscous liquid by naked eyes. The change in hue was evaluated according to the following ratings:

A: Substantially no change in hue as compared to that of the blank; and

B: Brown discoloration was apparently observed.

The evaluation results are collectively shown in Table 2.

TABLE 2

| | | Examples | |
|---|---|---|---|
| Items | 1 | 2 | 3 |
| Composition | | | |
| Fatty acid | Fatty acid A | Fatty acid B | Fatty acid A |
| Monovalent basic compound | Sodium hydroxide | Potassium hydroxide | Sodium hydroxide |
| Molar ratio of fatty acid/basic compound | 0.98 | 0.96 | 0.94 |
| Calcium salt or magnesium salt | Calcium chloride | Calcium chloride | Magnesium sulfate |
| Abbreviation symbol of metal soap | Y-1 | Y-2 | Y-3 |
| Analysis results | | | |
| (A) Metal content (mass %) | 6.8 | 8.6 | 4.0 |
| (B) Free fatty acid (mass %) | 0.1 | 0.8 | 0.9 |
| (C) Loss in weigh on drying (mass %) | 2.7 | 2.8 | 3.5 |
| (D) pH of water dispersion | 6.9 | 6.3 | 6.5 |
| (F) Average particle size (μm) | 19.3 | 24.5 | 15.4 |
| Evaluation of performance | | | |
| (F-1) Moldability | A | A | A |
| Anti-discoloration property | A | A | A |
| (F-2) Moldability | A | A | A |
| Keeping property | A | A | A |
| (G) Fluidity | A | A | A |
| Change in hue | A | A | A |

| | Comparative Examples | | |
|---|---|---|---|
| Items | 1 | 2 | Blank |
| Composition | | | |
| Fatty acid | Fatty acid A | Fatty acid A | No addition of metal soap |
| Monovalent basic compound | Sodium hydroxide | (direct method) | |
| Molar ratio of fatty acid/basic compound | 1.05 | | |
| Calcium salt or magnesium salt | Calcium chloride | Calcium hydroxide | |
| Abbreviation symbol of metal soap | Z-1 | Z-2 | |
| Analysis results | | | |
| (A) Metal content (mass %) | 6.9 | 6.5 | |
| (B) Free fatty acid (mass %) | 0.1 | 4.8 | |
| (C) Loss in weight on drying (mass %) | 2.7 | 2.8 | |
| (D) pH of water dispersion | 10.8 | 10.1 | |
| (F) Average particle size (μm) | 18.9 | 63.8 | |

TABLE 2-continued

Evaluation of performance

| | | | | |
|---|---|---|---|---|
| (F-1) | Moldability | A | B | C |
| | Anti-discoloration property | C | C | A |
| (F-2) | Moldability | A | B | C |
| | Keeping property | C | C | A |
| (G) | Fluidity | A | B | C |
| | Change in hue | C | C | A |

INDUSTRIAL APPLICABILITY

When the metal soap for a food additive according to the present invention is added to a food powder, the resultant mixture can be molded into tablets, etc., without defects such as creaking during molding of tablets, etc., and sticking and capping on the surface of each tablet. In addition, even after the foods are preserved at a temperature of 23° C. and a relative humidity of 50% RH for two months, substantially no discoloration on an appearance thereof is observed. Therefore, when forming the foods into tablets, etc., the metal soap of the present invention can be effectively used as a food additive for these foods which are required to exhibit good moldability, anti-discoloration property and keeping property (anti-color change property).

Further, in the application field of a food powder requiring a good fluidity which is used as a raw material in food-processing processes, when the metal soap for a food additive according to the present invention is added thereto, the resultant food powder can be enhanced in fluidity, can be prevented from undergoing troubles such as bridging and is free from discoloration due to heating. Therefore, the metal soap of the present invention can be considerably effectively utilized for food production using such a food powder.

In addition, in the process for producing a metal soap according to the present invention, the above-mentioned metal soap for a food additive can be produced in a stable manner with a high yield.

The invention claimed is:

1. A metal soap for a food additive comprising a fatty acid calcium salt or a fatty acid magnesium salt having 6 to 24 carbon atoms, wherein the fatty acid calcium salt or a fatty acid magnesium salt is produced by (1) reacting a fatty acid with a basic compound in an aqueous medium at such a molar ratio in which the basic compound is used in an amount of not less than 0.93 mol but less than 0.98 mol per 1 mol of the fatty acid to obtain a fatty acid basic compound salt, and (2) reacting the fatty acid basic compound salt with a water-soluble neutral calcium salt or a water-soluble neutral magnesium salt to obtain the fatty acid calcium salt or the fatty acid magnesium salt, and wherein a water dispersion containing said metal soap in an amount of 2% by mass exhibits a pH of not less than 6 but less than 7.

2. A process for producing a metal soap for a food additive comprising a fatty acid calcium salt or a fatty acid magnesium salt having 6 to 24 carbon atoms said process comprising: reacting 1 mol of a fatty acid having 6 to 24 carbon atoms with not less than 0.93 mol but less than 0.98 mol of a basic compound in an aqueous medium to obtain a fatty acid basic compound salt; and reacting the fatty acid basic compound salt with a water-soluble neutral calcium salt or a water-soluble neutral magnesium salt to obtain the fatty acid calcium salt or the fatty acid magnesium salt, wherein a water dispersion containing said metal soap in an amount of 2% by mass exhibits a pH of not less than 6 but less than 7.

3. The metal soap for a food additive according to claim 1, wherein the fatty acid calcium salt or the fatty acid magnesium salt has 12 to 22 carbon atoms.

4. The metal soap for a food additive according to claim 1, wherein the metal soap comprises a fatty acid calcium salt, and the fatty acid is reacted with the basic compound at such a molar ratio in which the basic compound is used in an amount of 0.95 to 0.98 mol per 1 mol of the fatty acid.

5. The metal soap for a food additive according to claim 1, wherein the metal soap comprises a fatty acid magnesium salt, and the fatty acid is reacted with the basic compound at such a molar ratio in which the basic compound is used in an amount of 0.93 to 0.96 mol per 1 mol of the fatty acid.

6. The metal soap for a food additive according to claim 1, wherein said pH is 6.3 to 6.9.

7. The metal soap for a food additive according to claim 1, wherein a concentration of the fatty acid basic compound salt in a reaction system is 1 to 20% by mass.

8. The metal soap for a food additive according to claim 7, wherein said concentration is 5 to 15% by mass.

9. The metal soap for a food additive according to claim 1, wherein said fatty acid is a linear fatty acid, and said basic compound is a monovalent basic compound.

10. The metal soap for a food additive according to claim 9, wherein the linear fatty acid is a linear saturated fatty acid having 12 to 22 carbon atoms, and said monovalent basic compound is selected from the group consisting of monovalent alkali metal hydroxides and ammonium compounds.

11. The metal soap for a food additive according to claim 10, wherein said monovalent basic compound is selected from the group consisting of sodium hydroxide and potassium hydroxide.

12. The metal soap for a food additive according to claim 1, wherein metal soap has having properties such that it can be used as a food additive.

13. The metal soap for a food additive according to claim 1, wherein the water-soluble neutral calcium salt and the water-soluble neutral magnesium salt are selected from the group consisting of calcium chloride, magnesium chloride, calcium nitrate and magnesium sulfate.

14. The metal soap for a food additive according to claim 13, wherein the water-soluble neutral calcium salt and the water-soluble neutral magnesium salt are selected from the group consisting of calcium chloride, calcium nitrate and magnesium sulfate.

* * * * *